United States Patent [19]
Sutter

[11] 3,972,122
[45] Aug. 3, 1976

[54] DENTAL ROUTER
[76] Inventor: James E. Sutter, Rte. No. 7, Box 177, Hot Springs, Ark. 71901
[22] Filed: Feb. 18, 1975
[21] Appl. No.: 550,551

[52] U.S. Cl. ............................................. 32/40 R
[51] Int. Cl.² ......................................... A61C 3/03
[58] Field of Search ................. 81/9.22; 51/170 TL; 310/29; 32/40 R, 53, 54, 52, 50; 128/305.1

[56] References Cited
UNITED STATES PATENTS

| | | | |
|---|---|---|---|
| 2,346,474 | 4/1944 | Torre | 310/17 X |
| 2,876,537 | 3/1959 | Bates | 310/29 |
| 2,984,241 | 5/1961 | Carlson | 32/53 |

*Primary Examiner*—Robert Peshock
*Attorney, Agent, or Firm*—Ralph R. Pittman

[57] ABSTRACT

A dental instrument for cutting and vibrating the stone loose from dentures, the device comprising an electrical implement in which electrical current moves a vibrating magnet iron at a very high speed so as to cause a forward extending piston that cuts and vibrates the stone loose.

3 Claims, 1 Drawing Figure

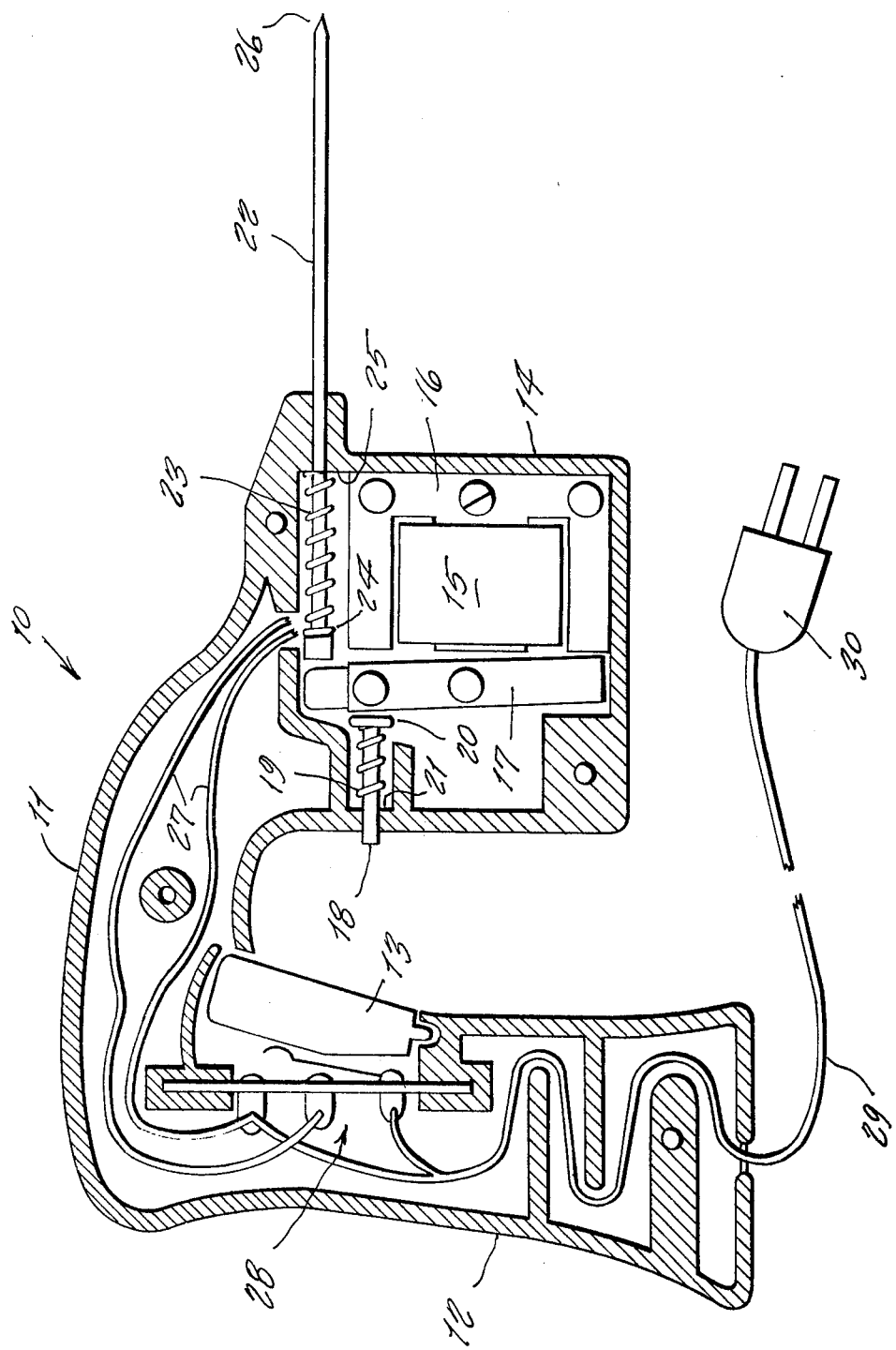

DENTAL ROUTER

This invention relates generally to dental apparatus.

A principal object of this invention is to provide a dental router which is used to cut and vibrate stone loose from dentures.

Another object of the present invention is to provide a dental router which is not likely to break dentures while operating thereupon.

Still a further object of this invention is to provide a dental router which is not likely to spring the partials when digging out the stone.

Still another object of the present invention is to provide a dental router which saves considerable time accomplishing its intended task.

Other objects are to provide a dental router which is simple in design, inexpensive to manufacture, rugged in construction, easy to use and efficient in operation.

These and other objects will be readily evident upon a study of the following specification and the accompanying drawing wherein:

The sole FIGURE is a side cross-sectional view of the present invention so to illustrate the interior construction thereof.

Referring now to the drawing in detail, the reference numeral 10 represents a dental router according to the present invention wherein there is a case 11 that is in the general shape of a hand gun by including a hand grip portion 12 for being grasped by a hand, and which includes a trigger 13 for being engaged by a finger of the hand that holds the handle grip portion. The case also includes a working head 14 from which the intended work is produced.

Within the interior of the head 14 there is contained a coil 15 having a main magnet iron 16 positioned forwardly thereof and a vibrating magnet iron 17 located rearwardly thereof. A rear piston 18 is slidably supported by the case 11, a forward end of the rear piston abutting against a rear edge of the vibrating magnet iron 17. A compression coil spring 19 bears at one end against a head 20 of the rear piston and at its other end bears against a rear wall 21 of the case through which the rear piston extends.

A front piston 22 is slidably supported through the head 14 of the case 11, a rear end of the front piston being aligned so to be effected by the vibrating magnet iron 17. A compression coil spring 23 bears at one end against a head 24 on a rear end of the front piston 22, the other end of the spring bearing against a front wall 25 through which a forward end of the front piston extends a substantial distance, the forward end of the front piston being tapered to a point 26.

Electrical wiring 27 extends from the coil 15 through the interior of the case 11 and into the handle portion 12 wherein there is a switch unit 28 that is activated by the trigger 13. An extension cord 29 extends outwardly of the end of the handle portion of the case, the outward end of the extension cord being fitted with a male plug 30 for connection to a household electric outlet supply, the other end of the extension cord being connected to the electric circuit of the switch unit and the coil.

In operative use, when electric current is turned on, the coil creates a magnetic field which passes through the main magnet iron 16 and the vibrating armature 17, thus pulling the two together, and since the front piston spring 23 and rear piston spring 19 are balanced with exact tension required by both, the vibrating armature 17 moves back and forth at a very high rate of speed, bouncing off of the rear piston 18 and the front piston 22. This action causes the chisel end 26 or otherwise pointed end of the front piston to cut and vibrate the stone loose from the dentures.

Thus is provided a dental router that performs a useful task and accomplishes the same in a better manner and in a quicker length of time.

While various changes may be made in detailed construction, it is understood that such changes will be within the spirit and scope of the present invention as is defined by the appended claims.

What I claim is:

1. In a dental chipper which includes a generally pistol-shaped casing, a reciprocably endwise movable vibrating chipping member projecting forwardly from said casing and an electromagnetic driver within said casing effective to actuate said chipping member, the improvement wherein:

said casing includes a hollow pistol grip portion having a transversely extending lower wall, a forwardly extending hollow neck portion merging with the upper end portion of said pistol grip portion and means defining a forwardly positioned chamber depending from the forward end of said neck portion, the cavities of said pistol grip portion and said neck portion merging to provide a continuous passageway from said lower wall of said pistol grip portion to said chamber, said chamber being disposed forwardly from said pistol grip portion to define a space therebetween at an elevation above the underside of said chamber for receiving an operator's hand embracing said pistol grip portion, and a top wall of said chamber being interposed between the cavity therein and the cavity within said neck portion, a reciprocably movable armature associated with said driver, a resiliently mounted rear piston disposed in the path of movement in one direction of said armature and spring means mounted on said chipping member continuously urging the rearward end thereof into the path movement of said armature in the opposite direction, said electromagnetic driver being enclosed within said chamber and said chipping member extending forwardly from said driver through an opening in the forward wall of said chamber spatially subjacent to the top wall thereof, and conductor means extending from said driver along said passageway to the outside of said casing at an aperture in the lower wall of said pistol grip portion.

2. The dental chipper as claimed in claim 1, wherein switch means is interposed in said conductor means within the cavity of said pistol grip portion of said casing and a rockable trigger member project forwardly from said pistol grip portion and movable inwardly into said cavity for actuating said switch means.

3. The dental chipper in accordance with claim 1, wherein said passageway includes a plurality of spaced baffles projecting into the cavity of said pistol grip portion and a portion of the length of said conductor means engages said baffles in a serpentine configuration.

* * * * *